United States Patent [19]

Kiszel et al.

[11] Patent Number: 4,539,984
[45] Date of Patent: Sep. 10, 1985

[54] RESPIRATOR DEVICE PARTICULARLY FOR USE IN PERINATAL MEDICINE

[75] Inventors: János Kiszel; László Papp; László Nagy, all of Budapest, Hungary

[73] Assignee: Vas es Moszeripari Szovetkezet, Hungary

[21] Appl. No.: 444,598

[22] PCT Filed: Mar. 26, 1981

[86] PCT No.: PCT/HU81/00012
§ 371 Date: Nov. 19, 1982
§ 102(e) Date: Nov. 19, 1982

[87] PCT Pub. No.: WO82/03326
PCT Pub. Date: Oct. 14, 1982

[51] Int. Cl.³ ............................................. A61M 16/00
[52] U.S. Cl. ............................................. 128/204.23
[58] Field of Search ...................... 128/204.21, 204.22, 128/204.23, 725

[56] References Cited

U.S. PATENT DOCUMENTS

| | | | |
|---|---|---|---|
| 2,920,622 | 1/1960 | Steel | 128/202.25 |
| 3,357,428 | 12/1967 | Carlson | 128/204.23 |
| 3,611,178 | 10/1971 | McConnell | 128/204.23 |
| 3,972,327 | 8/1976 | Ernst et al. | 128/204.21 |
| 4,323,064 | 4/1982 | Hoenig et al. | 128/204.21 |
| 4,357,936 | 11/1982 | Ellestad et al. | 128/204.23 |

FOREIGN PATENT DOCUMENTS 1045883 10/1966 United Kingdom ........... 128/202.25

Primary Examiner—Henry J. Recla
Attorney, Agent, or Firm—Handal & Morofsky

[57] ABSTRACT

A respirator device especially for the respiratory treatment of new-born and inmate infants and for their adaptation to natural breathing. The device comprises oxygen and air ducts, means for adjusting the composition, temperature, humidity, and other parameters of the gas mixture, a patient junction, and pressure adjusting valve means coupled to the junction shunting the gas flow in the junction in such a way that the gas pressure is positive both during expiration and inspiration.

The respiration demand of the patient is sensed by a means responsive to pressure drops which controls a starting signal generator and a beat generator. The beat generator controls the valve means. The device can be adjusted to controlled respiration, controlled assisted respiration, inspected and assisted respiration, and continuous positive airway pressure modes, whereby it can be adapted to various respiratory diseases. In the inspecting modes a respiration stoppage detector senses the spontaneous inspirations and in response to a stoppage exceeding a predetermined waiting period, performs controlled respiration for a given period of time and starts an alarm.

5 Claims, 8 Drawing Figures

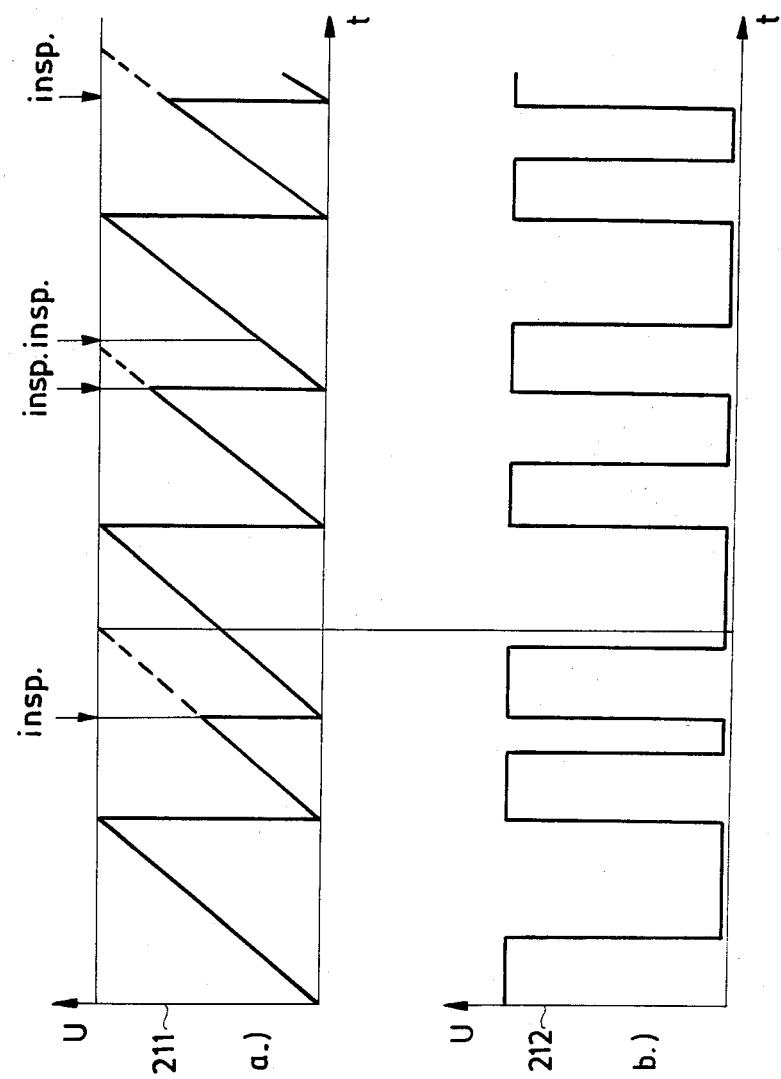

RESPIRATOR DEVICE PARTICULARLY FOR USE IN PERINATAL MEDICINE

FIELD OF THE INVENTION

The invention relates to a respirator device intended both for controlled breathing of new-born and premature infants or of laboratory animals and for making the infants to adapt to natural breathing, which device can be used in hospital wards as well as during transportation. The respirator comprises respective oxygen and air receiving ducts, means for adjusting the composition of the oxygen-air mixture, a conduit for transporting the mixture, a patient junction coupled to the conduit, a respiratory beat generator and pressure adjusting valve means controlled by the beat generator.

BACKGROUND ART

In the field of perinatal medicine there are a large number of diseases in which controlled respiration is required due to the lack or insufficiency of breathing. In a significant parts of cases requiring such respiration the problem is caused by some kinds of pulmonary malfunction, however, certain other types of diseases (e.g. paralysis of the breathing center,) also require controlled respiration. Of the respiratory problems of new-born and premature infants the idiopathical distress syndrome has a high incidence and it forms a major factor in perinatal mortality.

The controlled respiration raises in perinatal medicine a number of special demands which are different from normal respiratory practice. For that reason the miniaturization of conventional respiratory devices cannot solve the specific problems of perinatal respiratory diseases. Although there are already a number of respirator devices designed particularly for use in perinatal medicine, everyday practice has shown that they could not solve in general the problems in this particular field and they proved to be useful in comparatively narrow fields of indications only.

The handling of pneumatically controlled respirators designed for perinatal medicine is often inconvenient and such respirators cannot be used for the treatment of a number of respiratory problems. For example, one problem connected with such respirators lies in that the pressure of the expirated gas cannot be adjusted to the required values. According to another problem in the expirating periods, pressures below the atmospheric value might take place i.e., the respiration with continuous positive pressure and the respiration with alternating positive pressure cannot be implemented, although such kinds of respiration are considered to be necessary for the respiratory treatment of new-born infants.

The above summarized problems are also connected with respirators controlled electronically, because in such respirators the possibility of adjusting the pressure of expirated gas below the atmospheric value is also not excluded.

Apart from these main problems conventional respirators do not meet the complex requirements of perinatal respiration when their other facilities like handling capabilities, adjustability and the performance in various breathing modes are considered.

The practice in perinatal respiratorial therapy necessitates that the mode of respiration should be brought in correspondence with the type of the actual respiratory problem. Those kinds of respirator devices are required which can provide for a controlled mechanical respiration with alternating positive pressure if the lack or insufficiency of spontaneous breathing is detected. This can be effected by an atmospheric pressure at the ending phase of the expiration, or by adjusting a slight positive pressure at the end of the expiration. In many respiratory disturbances it is required that the spontaneously breathing new-born or inmate baby breathe from a continuously streaming oxygen-air mixture with positive pressure.

OBJECT OF THE INVENTION

The object of the invention is to provide a respirator device which can meet the complex demands of perinatal respiration and which can be capable of providing respiration in a perinatal ward or, if it is required, during transportation. The respirator device should have various modes of operation that enable the therapy of respiratory problems of new-born and inmate infants of different gravity and origin including the specific perinatal diseases like the idiopathic respiratory distress syndrome. In addition, the device should be able to make the baby leave off respiratory treatment under inspected breathing.

SUMMARY OF THE INVENTION

According to the invention a respirator device has been provided, especially for the respiratory treatment of new-born and inmate infants which comprises respective oxygen and air receiving ducts, means for adjusting the composition of the oxygen-air mixture, a conduit for transporting the mixture, a patient junction coupled to the conduit, a beat generator for determining the rhythm of breathing, and pressure adjusting valve means controlled by the output of the beat generator, in which according to the invention the respirator comprises a respiration demand detector with an input coupled to the patient junction and capable of detecting the pressure drop caused by the air intake of the patient during the expiration period of the device, a starting signal generator which in response to the detected pressure drop generates a corresponding starting pulse, a mode controller for adjusting the operational mode according to the actual requirement of the treatment, the beat generator comprises a generator unit provided with respective control inputs for the selection of continuous, triggered and retriggered modes of signal generation, the mode controller is used to couple the required one of these inputs to the output of the starting signal generator, and the pressure adjusting valve means is coupled to the patient junction and provides adjustable positive pressures both in inspiration and expiration at the junction by the controlled release of the oxygen-air mixture in the atmosphere.

In a preferable embodiment the output of the starting signal generator is coupled to the input of a respiration stoppage detector for providing an appropriate signal when no output pulse is received from the starting signal generation within a predetermined period of time, and this signal is coupled by the mode controller to the beat generator.

The respirator device according to the invention can be used in four basic modes of operation, i.e., controlled respiration for use in the absence of spontaneous breathing; controlled assisted respiration intended for use in the occurrence of repeated spontaneous breathing; inspected and assisted respiration which can be used after the formation of sufficient spontaneous breathing; and the inspected continuous positive airway pressure mode for use in respiratory therapy.

The invention is based on the particular way of watching the spontaneous inspiration of the patient and on the specific reaction generated in response thereto. The watching operation is carried out by the respiration demand detector, made preferably of a pressure difference—capacitance converter utilizing a metal membrane, in which a reference pressure is established in accordance with the preadjusted expiration pressure.

The respirator device according to the invention is capable of providing the new-born infant suffering from a respiratory disease with the required amount of streaming ionized gas to its trachea, which gas is fresh, having adjustable composition, humidity and inspiration and expiration pressure with controlled rate and duty cycle, and owing to its various adjustable modes of operation it provides a possibility for making the patient leave off instrumental respiration in such a way that a smooth transition is provided towards the normal breathing in the atmospheric air.

DESCRIPTION OF THE DRAWINGS

FIG. 8 illustrates in diagrammatic form the restarting operation of the generator in controlled assisted mode.

DETAILED DESCRIPTION OF THE INVENTION

Figure 1:
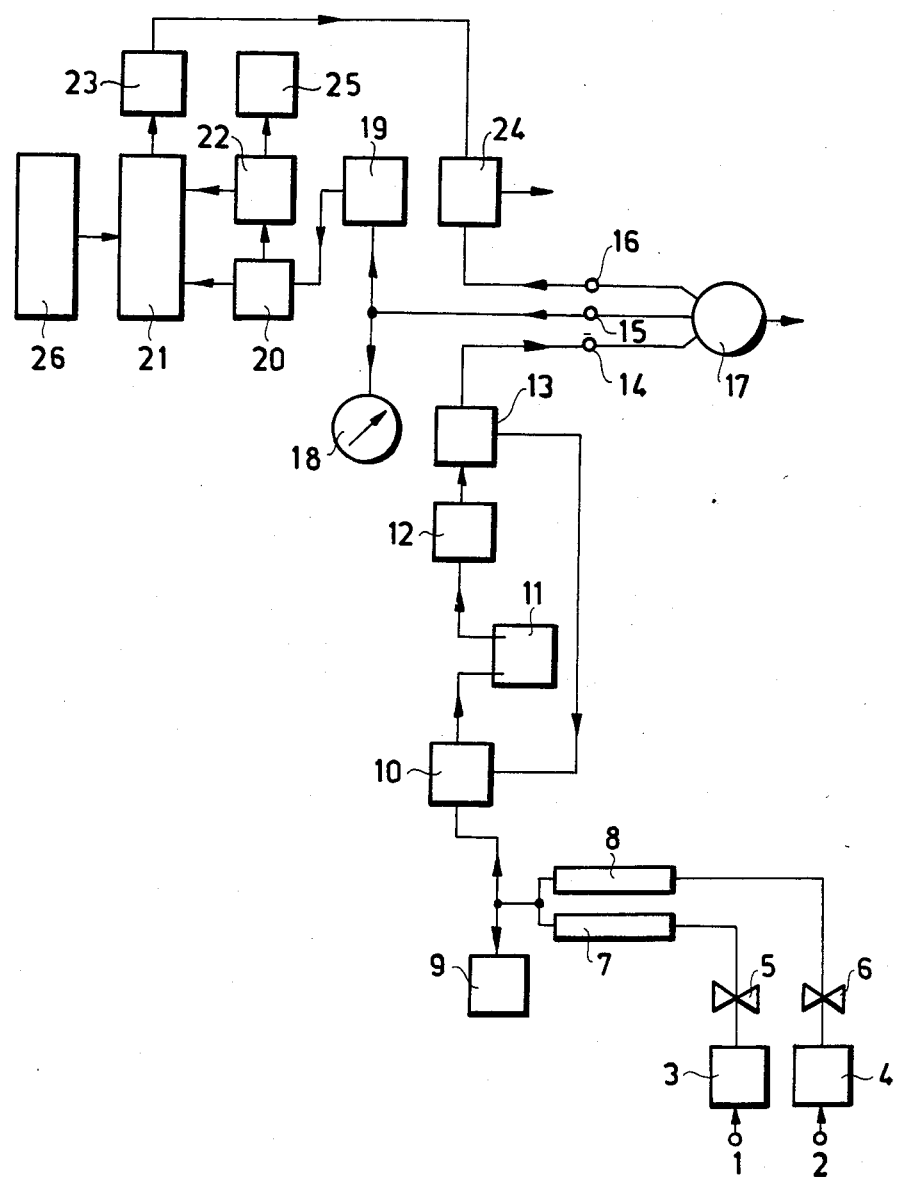
FIG. 1 shows the general block diagram of the respiratory apparatus according to the invention.

Reference is made now to FIG. 1 showing the general block diagram of the respirator according to the invention. Oxygen stored in a predetermined overpressure is lead to the respirator through oxygen receiving duct 1 and pressurized air is coupled to the respirator through an air receiving duct 2. The output of the oxygen receiving duct 1 is connected through an oxygen filter 3, a pin valve 5, and a flow meter 7 to a common conduit used for the transportation of oxygen-air mixture. Similarly, the air receiving duct 2 is connected to the same conduit through an air filter 4, a pin valve 6, and a flowmeter 8.

A safety valve 9 is coupled to the common conduit for preventing the establishment of pressures above a predetermined maximum value. The common conduit passes a gas-mixture heater 10, means 11 for adjusting the relative humidity of the mixture, and an ionizer 12, by which the mixture can be adjusted to a required temperature and humidity and it can also be ionized. The temperature of the gas leaving the ionizer 12 is sensed by a temperature detector 13 which generates an analogue electrical temperature control signal coupled to the control input of the gas-mixture heater 10.

The conduit of the oxygen-air mixture is coupled through a connection 14 to a patient junction 17 and the latter is formed substantially by a closed little room communicating with four openings. The first opening is connected to the connection 14 for receiving the over-pressurized oxygen-air mixture. The second opening is connected to a second connection 15, through which it is coupled to a manometer 18 and to a respiration demand detector 19. The third opening is coupled through a connection 16 to pressure adjusting valves 24. The oxygen-air mixture is released through the valves 24 to the free atmosphere under predetermined pressure values. The pressure prevailing in the respirator is determined by the condition of the valves 24. The fourth opening of the patient junction 17 is connected through a suitably designed flexible tube to the respiratory system of the new-born or of the patient under treatment.

The respiration demand detector 19 is designed substantially as a pressure-capacitance transducer, which is capable of converting the pressure changes occurring in the patient junction 17 relative to a predetermined reference pressure value into a capacitance change. An exemplary embodiment of the respiration demand detector 19 will be described in connection with FIG. 2.

The output of the respiration demand detector 19 is coupled to a starting signal generator 20 which senses the pressure drop caused by the spontaneous intake of air by the new-born and generates a starting signal. The output of the starting signal generator is coupled to a beat generator 21 and to a respiration stoppage detector 22. In certain modes of operation of the respirator the respiration stoppage detector 22 senses if the spontaneous breathing of the new-born has stopped throughout a given period of time, and in such conditions it generates a signal for the beat generator 21 and for an alarming device 25.

The beat generator 21 is adapted to adjust the parameters of the respiratory cycles and a mode controller 26 is used for setting the mode of operation of the beat generator 21. The output of the beat generator 21 is coupled through an amplifier 23 to the control input of the pressure adjusting valves 24 and provides for the appropriate control of the valves.

Figure 2:
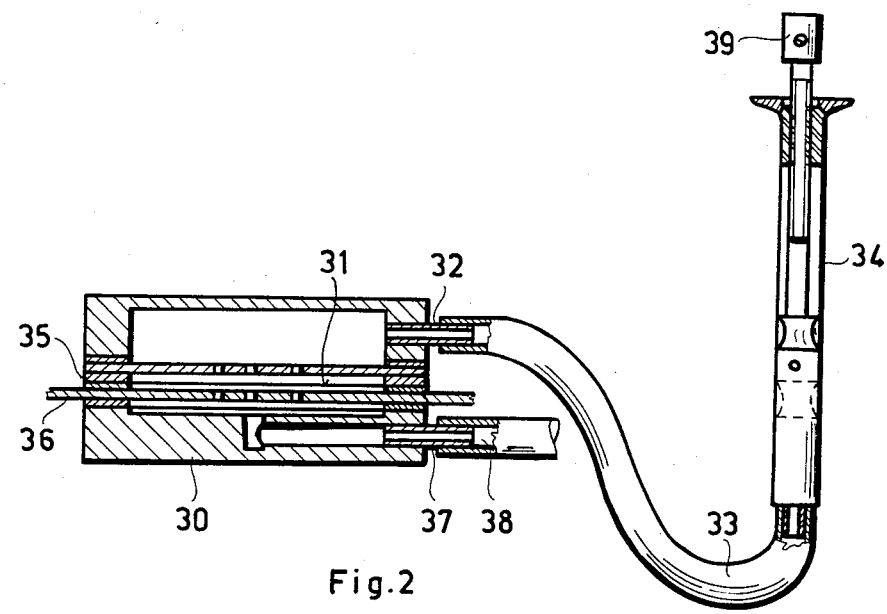
FIG. 2 shows the respiration demand detector in sectional elevation view.

Now reference will be made to FIG. 2 in which the structural design of a preferable embodiment of the respiratory demand detector 19 is shown. The respiratory demand detector comprises a case 30 defining a cylindrical inner room divided into two parts by a metal membrane 31. The upper part comprises a duct 32 connected to conduit 33 through which the inner room is coupled to a pressure adjusting assembly 34 adapted to set a required overpressure for reference purposes. A disc 35 is arranged in the case 30 spaced above the metal membrane 31 and is provided with a plurality of perforations. At the other side of the metal membrane 31 opposite to the disc 35 another disc 36 is provided which also has perforations and on the surface of the disc 36 that faces the membrane 31 an electrically conductive coating is provided. The metal membrane 31 and the disc 36 together form a capacitor and the two terminals thereof are coupled to the input of the starting signal generator 20 (FIG. 1). The lower space of the case 30 communicates through a duct 37 with a flexible tube 38 which is coupled to the manometer 18 and to the connection 15 of the patient junction 17.

The pressure adjusting assembly 34 comprises a piston displaceable in a cylindrical house and its axial displacement is adjusted by a threaded knob 39 by which the pressure acting on the upper side of the metal membrane 31 can be set to the desired value. During operation of the respirator a slightly increased pressure compared to the atmospheric one (e.g. 0.4 to 0.5 kPa) is established in the respiratory system of the patient even in the expiration phase, and the pressure adjusting assembly 34 is used to establish a reference pressure in the spacce above the metal membrane 31 which is lower by about 0.05 kPa than the required expiration pressure If the new born provides a pressure-drop higher than this 0.05 kPa value during inspiration in the interior of the patient junction 17, then the pressure below the metal membrane 31 will be smaller than that prevailing above the membrane 31, and the pressure in the upper part established by the pressure adjusting assembly 34 displaces the metal membrane 31 towards the lower disc 36, whereby the capacitance of the above mentioned capacitor will be increased.

New reference will be made to FIG. 3 in which the units used for adjusting the parameters of the respiration is shown in detail. The two terminals of the pressure-sensing capacitor of the respiration demand detector 19 are coupled to the inputs of an astable multivibrator 201 that define the duty cycle thereof. Another astable multivibrator 202 is running together with the first astable multivibrator 201 which has the same nominal frequency and fixed duty cycle. The two multivibrators are synchronized in such a way that each of their periods is started at the same moment. The outputs of the astable multivibrators 201 and 202 are coupled to respective inputs of a logical gating circuit 203 formed expediently by a half antivalence gate, and the output of the gating circuit 203 is coupled to an integrating circuit 204. The above circuits form together the starting signal generator 20 shown in FIG. 1. Before discussing the other parts of the apparatus in detail the generation of the starting signal will be explained in connection with FIGS. 4 and 5.

The astable multivibrator 202 generates constant frequency pulses with periods $T_1$ (FIG. 4a). The starting of the respective periods of the astable multivibrator 201 coincides with that of the multivibrator 202. It is supposed that before the moment $t_o$ no inspiration takes place and the width of the output pulses of the astable multivibrator 201 is smaller than that of the other multivibrator 202 (FIG. 4b). After the moment $t_o$ inspiration takes place, whereby the capacitance of the capacitor in the respiration demand detector 19 increases and this increase extends the width of the astable multivibrator 201. The astable multivibrator 201 is adjusted in such a way that the width of its output pulses reach the width of the pulses of the other multivibrator 202 when the pressure established by the inspiration of the new-born just equals the reference pressure set by the pressure adjusting assembly 34.

The logical 0 and 1 symbols shown in FIG. 4c illustrate the output variables at the outputs of the astable multivibrators 201 and 202 and of the logical gating circuit 203. The output of the gating circuit 203 is on logic 1 level only if the output of the astable multivibrator 201 is on 1 level and the output of the astable multivibrator 202 is on 0 level. This condition can take place during inspiration only. FIG. 5a illustrates the signals at the input of the integrating circuit 204 and FIG. 5b shows the integrator output.

Figure 4:
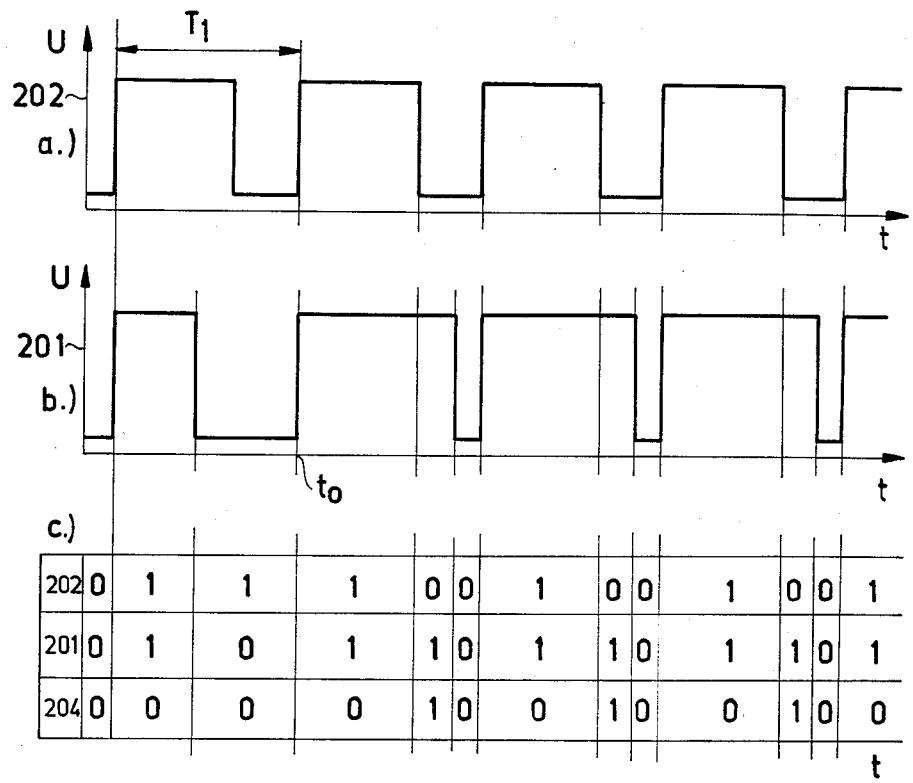
FIGS. 4 and 5 show signal condition curves measured in typical points of the starting signal generator.
Figure 5:
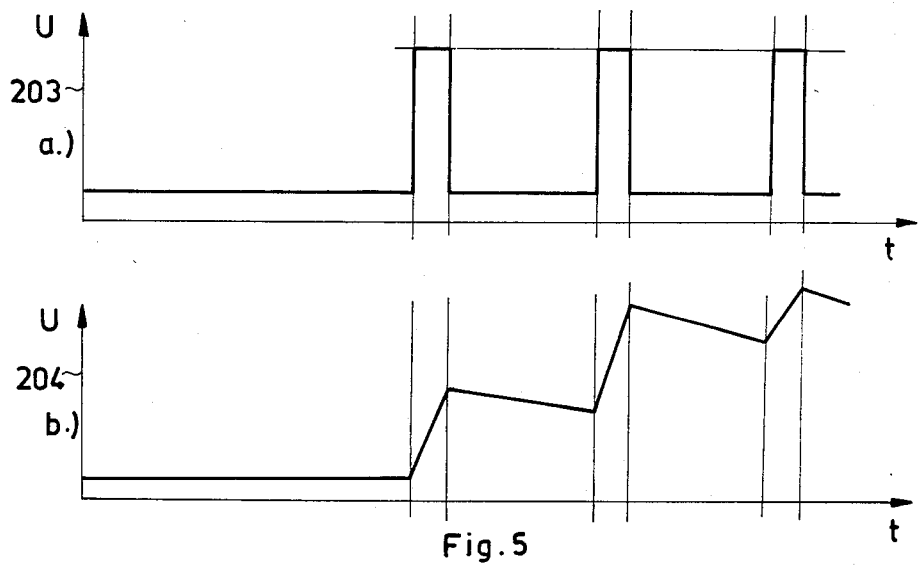

During the inspiration period of the newborn the gating circuit 203 provides respective output pulses in each period of the astable multivibrators 201 and 202, and the output signal of the integrating circuit 204 increases in a stepwise manner due to the integration of such output pulses. In FIGS. 4 and 5 an enlarged time scale is used compared to the respiration cycles, which means that the integrated pulse shown in FIG. 5b is very short compared to a respiratory cycle i.e., the integrator output produces practically immediately a pulse in response to the detection of the inspiration. The integration process is required for the elimination of random disturbances and for the sake of neglecting the insufficient inspiration efforts. All sufficient inspiration of the new-born is associated with the generation of a respective pulse.

Reference is made again to FIG. 3 in which it is illustrated that the output of the integrating circuit 204 is coupled, on the first hand, to the input of the respiration stoppage detector 22 (which can be, e.g., retriggerable monostable multivibrator), and on the other hand, to the input of a gating circuit 213. The gating circuit 213 comprises another input receiving the output of the respiration stoppage detector 22 and four other control inputs which, in accordance with the four operational modes, are coupled to the outputs of the mode controller 26. The gating circuit 213 has three output terminals driven in accordance with the selected mode of operation, and these output terminals are coupled to respective inputs of a sawtooth generator 211. The sawtooth generator 211 comprises a trigger input 214, a retriggered input 215, an astable input 216, and a frequency adjusting input 217. The frequency adjusting input 217 is coupled to a potentiometer (not shown) for setting the respiration frequency.

The output of the sawtooth generator 211 is coupled to the signal input of a comparator 212 which latter has a reference input 218 coupled to a potentiometer (not shown) adjusting the expiration-inspiration ratio.

The sawtooth generator 211, the comparator 212, and the gating circuit 213 form together the beat generator 21 shown in FIG. 1.

Figure 3:
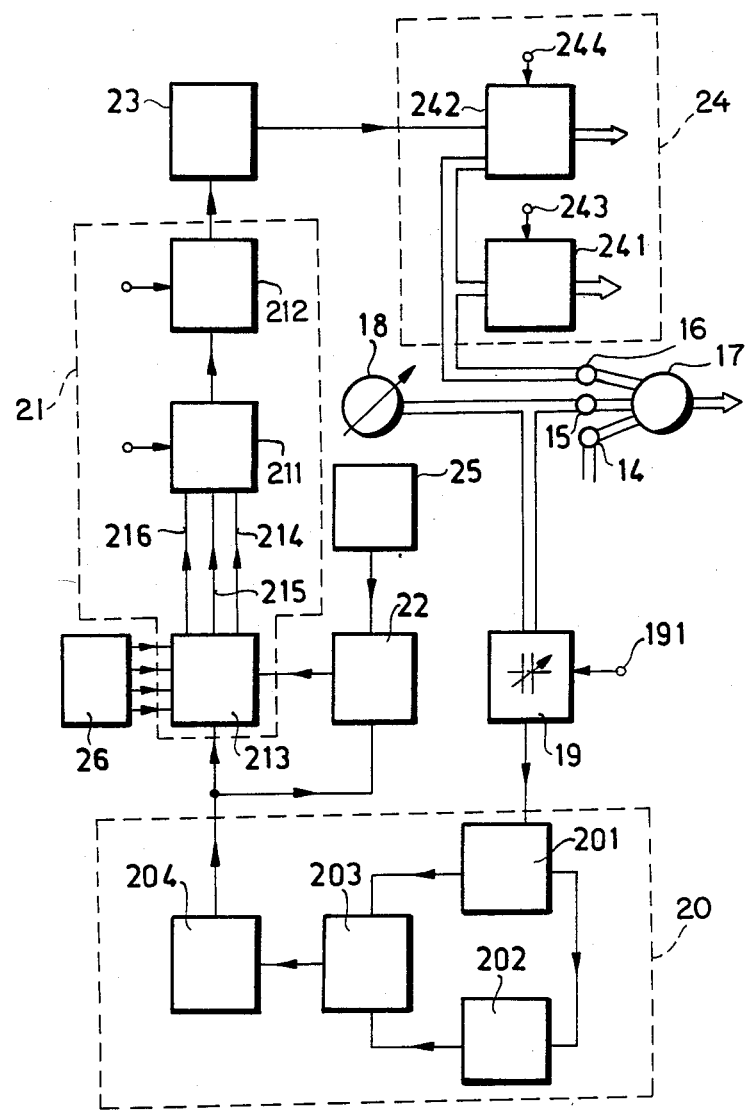
FIG. 3 is a more detailed block diagram of the electrical units of the respiratory apparatus.

FIG. 3 illustrates the pressure adjusting valves 24 consisting of an electrically controlled expiration valve 242 and a pneumatic inspiration valve 241. The valves 241 and 242 communicate with the free atmosphere, and the pressure threshold levels at which they let the gas mixture flow out to the free space can be adjusted within wide ranges by means of respective threshold adjustingg inputs 243 and 244.

When no control signal is generated by the amplifier 23, the path of the conduit coming from the connection 16 is open towards the expiration valve 242 and the comparatively low pressure threshold set for the expiration valve 242 determines the pressure prevailing in the system. This threshold level is typically 0.4 to 0.5 kPa higher than the normal atmospheric pressure. When a control signal is generated by the amplifier 23, the passage through the expiration valve 242 is cut off and the pressure in the system will be determined by the threshold level set for the inspiration valve 241 which corresponds typically to an overpressure or 1.5 to 2.5 kPa. The inspiration valve 241 is ineffective during expiration because the expiration valve 242 with its lower threshold level prevents the increase of pressure above that value.

Figure 6:
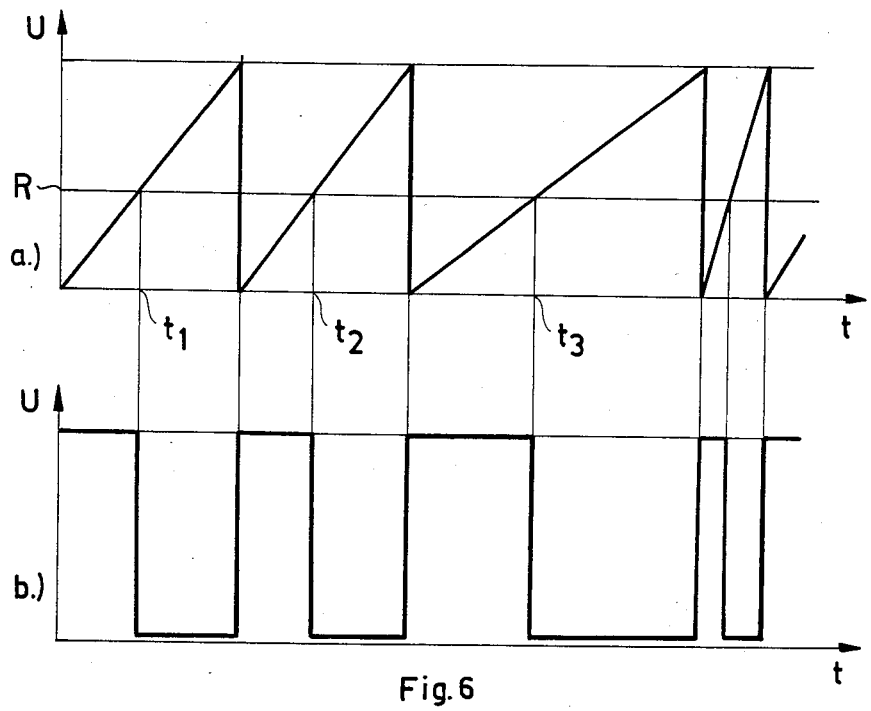
FIG. 6 shows signal curves measured in typical points of the beat generator.

The operation of the respirator according to the invention will be described in connection with the time diagrams shown in FIGS. 6 to 8.

It is true for all modes of operation that the respirator receives through the oxygen receiving duct 1 and the air receiving duct 2 oxygen and air with predetermined pressure from respective sources not shown in the drawing. The ratio of the oxygen and the air can be adjusted to desired values by the pin valves 5 and 6, and the rotational flowmeters 7 and 8 indicate the extent of the instantaneous gas flow. The adjustment of the temperature and the relative humidity of the gas mixture and the ionization of the same is carried out by the units shown in FIG. 1, whereby a sterilized gas mixture with predetermined temperature, humidity and composition will flow through the connection 14 towards the patient junction 17.

The respirator according to the invention can be operated by the mode controller 26 in four modes of operation.

The first mode is the controlled respiration which should be used in the absence of spontaneous breathing. In this mode the pressure of the streaming gas mixture is rhythmically changed between respective pre-adjustable inspiration and expiration pressure values. The number of breathing cycles as well as the ratio of expiration to inspiration can also be adjusted within wide ranges.

In this mode of operation the astable input 216 of the sawtooth generator 211 receives an enable signal, and the frequency of the sawtooth generator 211 can be set by an adjusting potentiometer not illustrated in FIG. 3, and the sawtooth generator 211 generates a continuous train of sawtooth signals. FIG. 6a shows the output of the sawtooth generator 211 and the reference level R of the comparator 212. When the increasing sawtooth signal reaches the reference level R, the comparator 212 is turned over (FIG. 6b) and the expiration period is started. The logical value 1 of the comparator output corresponds to inspiration and the logical value 0 corresponds to expiration. If the frequency of the sawtooth signals is changed, the ratio of the expiration period to the inspiration will not change. The moments $t_1$, $t_2$ and $t_3$ respectively indicate boundaries of time sections in the respective associated periods, in which the ratio of the expiration/inspiration sections is constant. Obviously, the expiration-to-inspiration ratio can be changed freely within wide limits by changing the reference level R, and the so-adjusted ratio is independent from the frequency setting.

Figure 7:
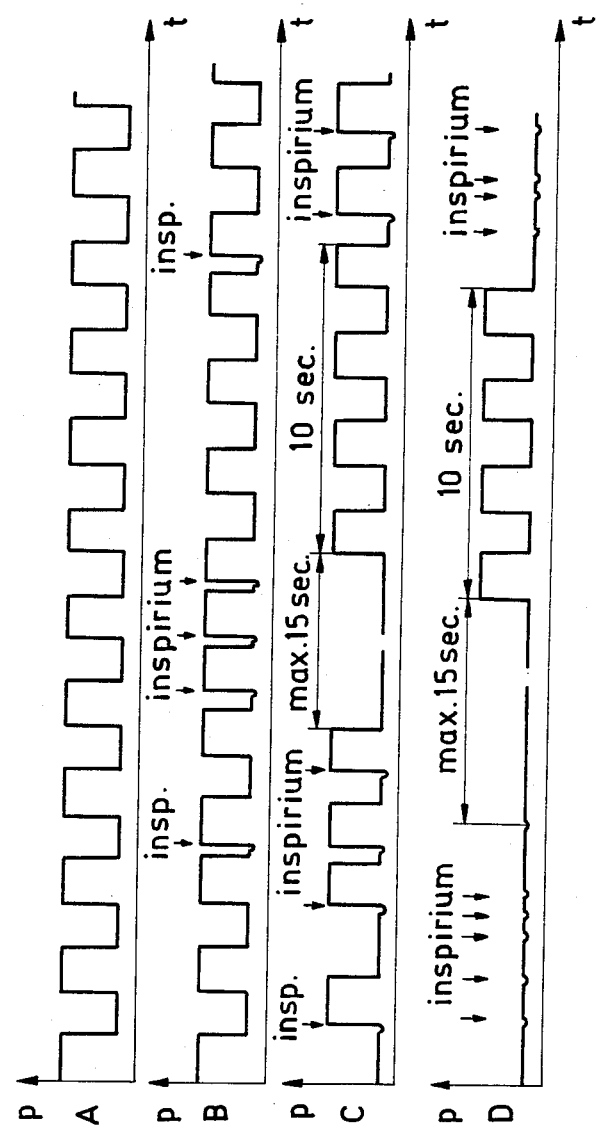
FIG. 7 shows the pressure versus time curves in all the four operational modes.

FIG. 7 shows the pressure versus time diagram for the controlled respiration mode A, and it can be seen that the pressure is changed independently from the breathing efforts of the new-born.

The second mode B is the controlled assisted respiration which is recommended when repeated spontaneous breathing is experienced. In this mode a controlled respiration takes place (diagram B in FIG. 7) and the respiration demand detector 19 is used to sense the moments when the patient begins breathing in. If such an inspiration is sensed (the moments of which being indicated by short vertical arrows in FIG. 7), the respirator is immediately switched over to inspiration, which means that the respirator is made to adapt itself to the breathing rhythm of the patient.

This process is illustrated in FIGS. 8a and 8b in detail. In the controlled assisted respiration position of the mode controller 26 the retriggered input 215 of the sawtooth generator 211 receives the enable signal. In this mode the sawtooth generator 211 oscillates continuously just as in the previous mode and the pressure in the system changes periodically according to the present values. In this mode, however, at each spontaneous inspiration a corresponding pulse is generated at the output of the integrating circuit 204. The gating circuit 213 passes the pulse associated with the spontaneous inspiration to the retriggered input 215 of the sawtooth generator 211, which in response to such control starts immediately a new sawtooth cycle. In FIG. 8a the short vertical arrows indicate the inspiration moments, and it can be seen that in response to such events a new cycle is started which always begins with an inspiration cycle. The demand of the patient for inspiration will therefore be immediately satisfied.

The third mode C of the respirator is the inspected and assisted respiration. This mode is preferable when during the therapy a sufficient spontaneous breathing is established. In this mode there is no controlled respiration with fixed frequency, and the rhythm of respiration is determined only by the inspiration demand of the patient. In diagram C of FIG. 7 the inspiration moments are illustrated by the short vertical arrows. Each inspiration is sensed by the respiration demand detector 19 and a corresponding starting pulse is generated by the starting signal generator 20.

A mode controller 26 controls now the gating circuit 213 to send the enable signal to the trigger input 214 of the sawtooth generator 211 and to establish a path between the output of the respiration stoppage detector 22 and the astable input 216 of the sawtooth generator 211. Sawtooth generation will take place only if the trigger input 214 receives a control signal from the output of the integrating circuit 204. This occurs always at the beginning of the spontaneous inspiration of the patient. In the starting period of the sawtooth generator 211 an inspiration begins which is followed by an expiration period which lasts until the next starting moment.

It can be seen in diagram C of FIG. 7 that each spontaneous inspiration is associated with the beginning of an inspiration period. The rhythm of the breathing is determined by the demand of the patient.

The inspecting function lies in that in every inspiration moment the respiration stoppage detector 22 starts a waiting period which is about 15 seconds long. If the subsequent inspiration occurs within the waiting period, then a new waiting period is started and the condition of the respiration stoppage detector 22 will not change. If the waiting period is finished and no inspiration occurs, it will change the logical condition of the respiration stoppage detector 22, and the astable input 216 of the sawtooth generator will be activated and a controlled respiration will take place according to the controlled respiration mode for a predetermined period of time. At the same time the respiration stoppage detector 22 controls the alarming device 25, whereby a sufficient alarm will be generated.

In diagram C of FIG. 7 the period $T_2$ shows the waiting period that corresponds to the maximum stoppage of the breathing. This is followed by the controlled respiration for a period $T_3$. This period $T_3$ lasts typically for 10 seconds and its value can be freely adjusted between appropriate limits. If a spontaneous breathing begins following the controlled respiration period, the assisted respiration will be continued.

The fourth mode of operation D of the respiration is the inspected continuous positive airway pressure CPAP. This mode D is very similar to the CPAP mode commonly used in respiratory therapy, in which the patient spontaneously breathes from the streaming gas mixture with positive pressure.

The difference compared to the conventional CPAP mode lies in the way of responding to a stoppage of spontaneous breathing. Contrary to the conventional modes, the inspection is not performed by the nursing personnel, but automatically by the inspection function of the respirator.

The mode controller 26 establishes now a path through the gating circuit 203 between the output of the respiration stoppage detector 22 and the astable input 216 of the sawtooth generator 211.

Owing to this constructional design, controlled respiration does not take place until a respiration stoppage is sensed and the sawtooth generator 211 is not running either. The inspiration of the patient is inspected in the way described earlier and at the beginning of each inspiration period the respiration stoppage detector 22 starts respective waiting periods $T_2$. In diagram D of FIG. 7 the inspiration moments are indicated by short vertical arrows. If no inspiration is sensed during the predetermined waiting period $T_2$, the respiration stoppage detector 22 enables the alarming device 25 and controls the sawtooth generator 211 to start astable oscillation for a period $T_3$. As a result of this control a controlled respiration will take place for a period of 10 seconds, whereafter the respirator returns to the CPAP mode and to the inspection of the respiration.

It can be seen from the above description of the respirator according to the invention that besides its simple circuit design, it can be used quickly and effectively in any kind of respiratory disturbances. With the above-described design the respirator cannot establish pressure less than the atmospheric value.

The construction of the respirator according to the invention can be realized in small sizes in portable casing and it can also be arranged in an incubator. The application of such a respirator provides for the possibility of gas sterilization when the respiration is in assembled condition and it provides also for the appropriate setting of the composition, temperature and humidity of the gas mixture, for its ionization and for the adjustment of required respiratory parameters.

We claim:

1. A respirator device, particularly for the respiratory treatment of new-born and inmate infants, comprising an oxygen (1) and an air (2) duct coupled respectively to a source of oxygen and pressurized air, a mixing conduit for receiving said oxygen and air, valve means (5, 6) for adjusting the oxygen-air ratio of said mixture, a conduit coupled to said valve means conducting said mixture, a patient junction (17) coupled to said conduit, a controlled beat generator (21) for determining the rhythm of breathing and having an output, a pressure adjusting valve means (24) controlled by the output of the beat generator (21) and coupled to the patient junction for providing adjustable positive pressure threshold levels both during the inspiration and expiration periods, a respiration demand detector (19) comprising an input and an output, said input of said demand detector is coupled to the patient junction (17) for detecting the pressure drop caused by the patient during inspiration, a starting signal generator (20) having an input connected to the output of the respiration demand detector (19) for generating a starting signal in response to the detected pressure drop of each detected inspiration, said starting signal generator (20) comprising an output, said beat generator (21) comprises a sawtooth generator (211) having a trigger input (214), a retriggered input (215) and an astable input (216) and an output wherein said trigger input (214) is associated with assisted respiration; said retriggered input (215) is associated with controlled assisted respiration, and said astable input (216) is associated with controlled respiration in absence of spontaneous breathing, a gating circuit (213) comprising three outputs each being coupled to a respective one of said inputs (214, 215, 216) of said sawtooth generator, said gating circuit (213) comprising an input connected to the output of the starting signal generator (20), a respiration stoppage detector comprising an input and output, said output of the starting generator (20) is connected also to said respiration stoppage detector (22) for sensing the presence of spontaneous breathing and for providing a signal in the absence of an output pulse from the starting signal generator (20) within a predetermined period of time, the gating circuit (213) comprises a plurality of enabling inputs, a mode controller (26) for the selection of the operational mode corresponding to the required treatment and having a plurality of outputs connected to respective outputs of said mode controller (26) and accordingly selecting an appropriate one of the trigger, retrigger or astable inputs (214, 215, 216) of the sawtooth generator (211) in accordance with the setting of said mode controller (26) set by the operator, a comparator (212), said pressure adjusting valve means (24) comprising a control input, said output of the sawtooth generator (211) is connected via said comparator (212) to said control input of said pressure adjusting valve means (24), wherein said demand detector (19) is formed by a membrane-operated pressure difference-to-capacitance transducer comprising a housing (30) divided by a metal membrane (31) into two chambers, a pressure adjusting assembly (34) is coupled to one of said chambers, the other chamber communicating with an interior of the patient junction (17), and wherein said pressure adjusting valve means (24) comprises a controlled expiration valve (242) having a control input coupled to the output of the beat generator (21) and a pneumatic input coupled to the patient junction (17) which in rest condition defining the expiration pressure, and an inspiration valve (241) having an input coupled to the patient junction (17) and in the on condition of the expiration valve (242) defining the inspiration pressure.

2. The respirator device as claimed in claim 1, wherein the respiration stoppage detector (22) is formed by a monostable multivibrator and having an input coupled to an alarm device (25) for generating a breathing stoppage alarm.

3. A respirator device, particularly for the respiratory treatment of new-born and inmate infants, comprising an oxygen (1) and an air (2) duct coupled respectively to a source of oxygen and pressurized air, a mixing conduit for receiving said oxygen and air, valve means (5, 6) for adjusting the oxygen-air ratio of said mixture, a conduit coupled to said valve means conducting said mixture, a patient junction (17) coupled to said conduit, a controlled beat generator (21) for determining the rhythm of breathing and having an output, a pressure adjusting valve means (24) controlled by the output of the beat generator (21) and coupled to the patient junction for providing adjustable positive pressure threshold levels both during the inspiration and expiration periods, a respiration demand detector (19) comprising an input and an output, said input of said demand detector is coupled to the patient junction (17) for detecting the pressure drop caused by the patient during inspiration, a starting signal generator (20) having an input connected to the output of the respiration demand detector (19) for generating a starting signal in response to the detected pressure drop of each detected inspiration, said starting signal generator (20) comprising an output, said beat generator (21) comprises a sawtooth generator (211) having a trigger input (214), a retriggered input (215)

and an astable input (216) and an output wherein said trigger input (214) is associated with assisted respiration; said retriggered input (215) is associated with controlled assisted respiration, and said astable input (216) is associated with controlled respiration in absence of spontaneous breathing, a gating circuit (213) comprising three outputs each being coupled to a respective one of said inputs (214, 215, 216) of said sawtooth generator, said gating circuit (213) comprising an input connected to the output of the starting signal generator (20), a respiration stoppage detector comprising an input and output, said output of the starting generator (20) is connected also to said respiration stoppage detector (22) for sensing the presence of spontaneous breathing and for providing a signal in the absence of an output pulse from the starting signal generator (20) within a predetermined period of time, the gating circuit (213) comprises a plurality of enabling inputs, a mode controller (26) for the selection of the operational mode corresponding to the required treatment and having a plurality of outputs connected to respective outputs of said mode controller (26) and accordingly selecting an appropriate one of the trigger, retrigger or astable inputs (214, 215, 216) of the sawtooth generator (211) in accordance with the setting of said mode controller (26) set by the operator, a comparator (212), said pressure adjusting valve means (24) comprising a control input, said output of the sawtooth generator (211) is connected via said comparator (212) to said control input of said pressure adjusting valve means (24), wherein said respiration demand detector comprises a case divided into first and second chambers by a metal membrane, a pressure adjusting assembly, said first chamber communicating with said pressure adjusting assembly and said second chamber communicating with said patient junction means, and further comprises a perforated disc located in said second chamber and confronting said metal membrane, said perforated disc being coated with electrically conductive material such that said metal membrane and said perforated disc comprise a capacitor.

4. A respirator as in claim 3, wherein changes in pressure in said second chamber produce corresponding changes in the capacitance of said capacitor, said capacitor being coupled to the input of said starting signal generator.

5. A respirator device, particularly for the respiratory treatment of new-born and inmate infants, comprising an oxygen (1) and an air (2) duct coupled respectively to a source of oxygen and pressurized air, a mixing conduit for receiving said oxygen and air, valve means (5, 6) for adjusting the oxygen-air ratio of said mixture, a conduit coupled to said valve means conducting said mixture, a patient junction (17) coupled to said conduit, a controlled beat generator (21) for determining the rhythm of breathing and having an output, a pressure adjusting valve means (24) controlled by the output of the beat generator (21) and coupled to the patient junction for providing adjustable positive pressure threshold levels both during the inspiration and expiration periods, a respiration demand detector (19) comprising an input and an output, said input of said demand detector is coupled to the patient junction (17) for detecting the pressure drop caused by the patient during inspiration, a starting signal generator (20) having an input connected to the output of the respiration demand detector (19) for generating a starting signal in response to the detected pressure drop of each detected inspiration, said starting signal generator (20) comprising an output, said beat generator (21) comprises a sawtooth generator (211) having a trigger input (214), a retriggered input (215) and an astable input (216) and an output wherein said trigger input (214) is associated with assisted respiration; said retriggered input (215) is associated with controlled assisted respiration, and said astable input (216) is associated with controlled respiration in absence of spontaneous breathing, a gating circuit (213) comprising three outputs each being coupled to a respective one of said inputs (214, 215, 216) of said sawtooth generator, said gating circuit (213) comprising an input connected to the output of the starting signal generator (20), a respiration stoppage detector comprising an input and output, said output of the starting generator (20) is connected also to said respiration stoppage detector (22) for sensing the presence of spontaneous breathing and for providing a signal in the absence of an output pulse from the starting signal generator (20) within a predetermined period of time, the gating circuit (213) comprises a plurality of enabling inputs, a mode controller (26) for the selection of the operational mode corresponding to the required treatment and having a plurality of outputs connected to respective outputs of said mode controller (26) and accordingly selecting an appropriate one of the trigger, retrigger or astable inputs (214, 215, 216) of the sawtooth generator (211) in accordance with the setting of said mode controller (26) set by the operator, a comparator (212), said pressure adjusting valve means (24) comprising a control input, said output of the sawtooth generator (211) is connected via said comparator (212) to said control input of said pressure adjusting valve means (24), wherein the starting signal generator (20) comprises a pair of synchronously started astable multivibrators (201, 202), the first astable multivibrator (201) comprises a control input for adjusting the duty cycle being coupled to the output of the respiration demand detector (19), said generator (20) comprises additionally a gating circuit (203) having respective inputs coupled to the outputs of the astable multivibrators (201, 202), and an integrating circuit (204) having an input coupled to the output of the gating circuit (203) and its output forming the output of the starting signal generator (20).

* * * * *